United States Patent [19]

Worden

[11] Patent Number: 4,991,883
[45] Date of Patent: Feb. 12, 1991

[54] CONNECTION APPARATUS

[75] Inventor: Raymond D. Worden, Houston, Tex.

[73] Assignee: Ruska Laboratories, Inc., Houston, Tex.

[21] Appl. No.: 411,929

[22] Filed: Sep. 25, 1989

[51] Int. Cl.$^5$ .............................................. F16L 25/00
[52] U.S. Cl. ................................ 285/334.4; 285/342; 285/348; 285/360; 285/375
[58] Field of Search ............ 285/342, 305, 348, 334.4, 285/343, 375, 267, 268, 269, 279, 360

[56] References Cited

U.S. PATENT DOCUMENTS

| | | | |
|---|---|---|---|
| 2,208,292 | 7/1940 | Hanson | 285/279 X |
| 4,281,679 | 8/1981 | Stearns | 285/342 X |
| 4,787,656 | 11/1988 | Ryder | 285/911 X |

*Primary Examiner*—Dave W. Arola
*Assistant Examiner*—Heather Chun
*Attorney, Agent, or Firm*—Browning, Bushman, Anderson & Brookhart

[57] ABSTRACT

An apparatus for connecting first and second conduits having first and second bores, respectively, to provide communication between the first and second bores. The apparatus includes a base attached to the first conduit and a cap attached to the base. A follower is slidably disposed in the cap and is provided with a passageway, the second conduit extending through the passageway. A ferrule is received on the second conduit, the ferrule having a first end and a second end. The follower is biased against the first end of the ferrule. The first bore in the first conduit has a frustoconical surface which defines a receiving formation for the ferrule, the ferrule having a portion which is circular when viewed in transverse cross section. When the second end of the ferrule is urged in the receiving formation by the action of the biasing spring, the ferrule engages the frustoconical surface defining the receiving formation in substantially line contact.

9 Claims, 1 Drawing Sheet

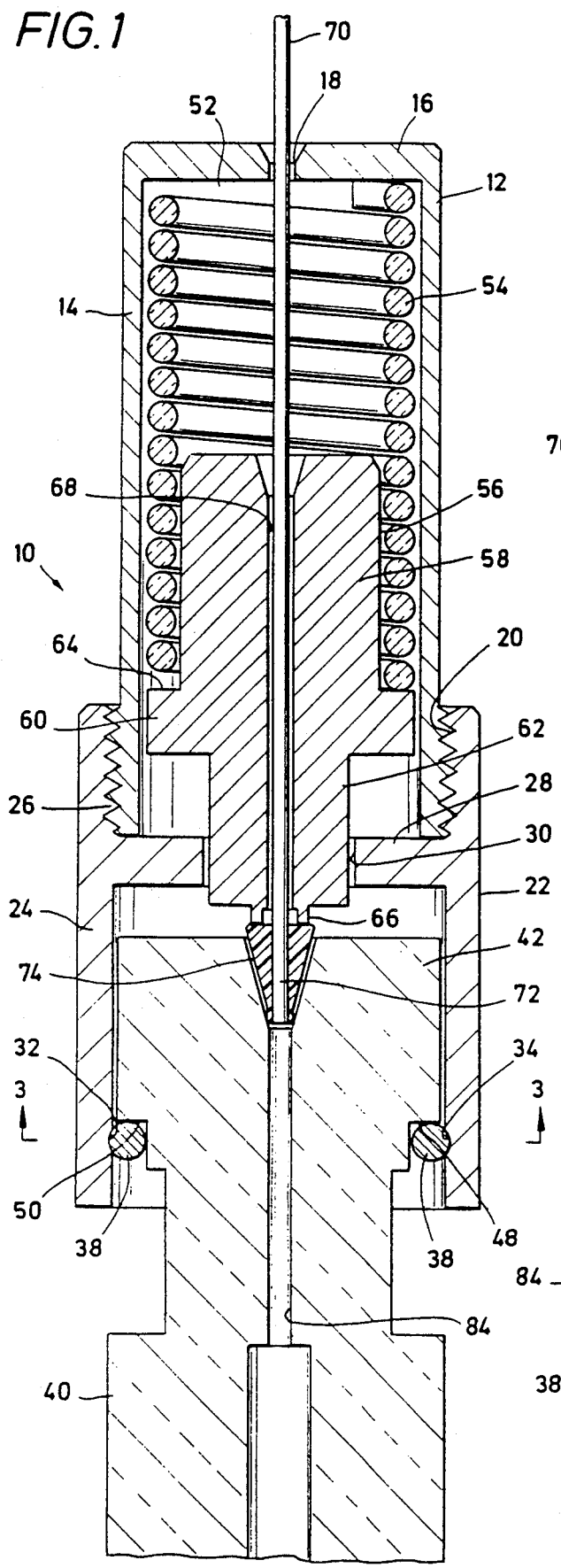
FIG.1
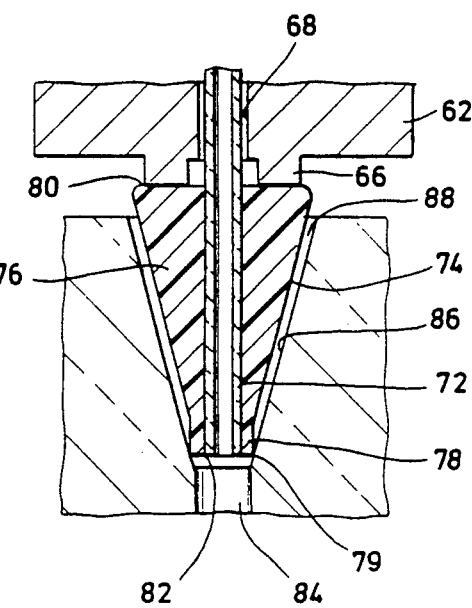
FIG.2
FIG.3

CONNECTION APPARATUS

BACKGROUND OF THE INVENTION

1. Field of the Invention

The present invention relates to an apparatus for effecting gas-tight communication between first and second members having bores for the passage of fluid. More particularly, the present invention relates to a high-temperatures, low-pressure connection for effecting fluid-tight communication between such members.

2. Description of the Background

There are numerous types of apparatus such as, for example, analytical instrumentation used in laboratories, chemical and refining plants and the like, which require connection of a first member through which is transported a fluid, such as a gas, to a second member, through which is transported the gas. In many cases, the connection is subject to extended, high temperatures, followed by periods of much cooler, even subfreezing temperature. The components of mechanical connections placed in this environment, because of the temperature swings, are subject to expansion and contraction with the result that eventually the connection is no longer gas-tight. For example, in the field of chemical analysis by pyrolysis or thermal degradation, extremely high temperatures are generally employed. Not only are such temperatures employed in the actual pyrolysis of the sample to be analyzed, but in the subsequent analysis of the thermally evolved products, it is generally necessary to maintain the temperature of the flow lines through which the evolved products flow at a high temperature in order to avoid their condensation prior to being sent to a suitable analyzer. Frequently in these systems, gas chromatographic analyzers are employed, and the flow lines and connectors are subject to these high temperatures and temperature swings.

SUMMARY OF THE INVENTION

It is therefore an object of the present invention to provide an improved connector for connecting first and second conduits.

Another object of the present invention is to provide a high temperature connector for connecting first and second conduits.

Still another object of the present invention is to provide an improved, high temperature connector for releasably connecting first and second conduits in fluid-tight communication with one another.

The above and other objects of the present invention will become apparent from the drawings, the description herein and the appended claims.

The apparatus of the present invention provides an apparatus for connecting a first conduit which has a first bore to a second conduit which has a second bore and thereby provide communication between the first and second bores. The apparatus includes a base and means to attach, preferably releasably, the base to the first conduit. There is also provided a cap with means to attach, preferably releasably, the cap to the base. A follower is slidably disposed in the cap, the follower having a passageway through which the second conduit extends. A ferrule is received on the second conduit, the ferrule being provided with a first end and a second end. Biasing means urge the follower against the first end of the ferrule. The first bore in the first conduit has a frustoconical surface defining a receiving formation for the ferrule. The ferrule has a portion which is circular when viewed in transverse cross section such that when the second end of the ferrule is urged in the receiving formation by the biasing means, the ferrule will engage the frustoconical surface defining the receiving formation in a substantially circular, line contact.

BRIEF DESCRIPTION OF THE DRAWINGS

FIG. 1 is an elevational view, partly in section, of the connecting apparatus of the present invention.

FIG. 2 is a portion of FIG. 1 enlarged for clarity.

FIG. 3 is a view taken along the lines 3—3 of FIG. 1.

DESCRIPTION OF PREFERRED EMBODIMENTS

While the present invention will be described with particular reference to a connector for use with a high temperature, gas chromatograph used as part of pyrolytic analysis system, it is to be understood that it is not so limited. The connecting apparatus of the present invention finds utility wherever it is desired to connect two flow conduits together in an environment where the connector is subjected to elevated temperature and/or large temperature swings.

Referring first to FIG. 1, the connector, shown generally as 10, includes a cap 12 having a cylindrical wall 14 and an end wall 16 with a generally centrally disclosed aperture 18 therein. The end of cylindrical wall 14 distal end 16 is provided with male threads 20.

Connector 10 further includes a base 22 having a generally cylindrical wall 24, one end of the cylindrical wall being provided with female threads 26 which mate with male threads 20 on cap 12 to allow cap 12 to be secured to base 22. Base 22 further includes an internal web 28 which has a generally centrally disposed, cylindrical bore 30 therethrough. The end of base 22 distal threads 26 is provided with throughbores 32 and 34 which are parallel to one another, the bores 32, 34 extending through the wall 24 of base 22 and intersecting the generally cylindrical cavity 36 formed by wall 24. Received in the bores 32, 34 are pins 38, pin 38 being frictionally held in bores 32, 34. It will thus be seen that pins 38 effectively form parallel chords as to the circular cross-sectional area defined by the interior surface of wall 24.

Base 22 cooperates with a first, fused quartz conduit 40 to form a bayonet mount whereby base 22 can be releasably and quickly attached to first conduit 40. To this end, first conduit 40 is provided with a head portion 42 which is formed from a generally cylindrical member from which has been removed chordal sections to provide parallel flats 44 and 46. Flats 44 and 46 have a chordal length L such that when the base 22 is rotated 90° from the position shown in FIG. 3, base 22 can be removed from first conduit 40. In contrast, in the position shown in FIG. 3, pins 38 prevent base 22 from being removed from first conduit 40 since they engage shoulders 48 and 50 formed on the head portion 42 of first conduit 40. It can thus be seen that a bayonet mount is formed between base 22 and first conduit 40 which allows rapid connecting and disconnecting of base 22 to and from conduit 40.

Disposed internally of cap 12 in the generally cylindrical cavity 52 formed therein is a quartz compression spring 54. Also, slidably disposed in the cylindrical cavity 52 formed in cap 12 is a follower 56, follower 56 having a first generally cylindrical portion 58, an intermediate, radially outwardly annular flange 60 and a second generally cylindrical portion 62, portion 62 being of reduced diameter relative to portion 58. Flange 60 forms an annularly extending shoulder 64. As shown, spring 54 is received between end wall 16 of cap 12 and annular shoulder 64 of follower 56. Accordingly, spring 54 will act to urge follower 56 away from end wall 16. An annular boss 66 projects axially outwardly from cylindrical section 62 of follower 56. A passageway 68 extends through follower 56, one end of the passageway 68 forming an opening which is generally centrally disposed with respect to annular boss 66. Extending through passageway 68 is a second conduit 70 which, in the case shown, is a quartz capillary tube. Second conduit 70 has an end portion 72 which projects outwardly past annular boss 66, a ferrule 74 being received on the end portion 72. Ferrule 74, which is generally of a deformable material is frictionally received on the end 72 of second conduit 70. Ferrule 74 includes a frustoconical portion 76 and a cylindrical neck portion 78 (see FIG. 2). Frustoconical portion 76 forms a first end 80 of ferrule 74 while cylindrical portion 78 forms a second end 82 of ferrule 74. It can thus be seen that ferrule 74 has a generally overall frustoconical configuration with the exception of the cylindrical neck portion 78 which has a diameter substantially equal to the smallest diameter of the frustoconical portion 76.

First conduit 40 includes a bore 84. Bore 84 is partially defined by frustoconical surface 86 which forms an opening for bore 84 out of first conduit 40 and, in general, defines a frustoconical receiving formation 88, ferrule 74 being received in receiving formation 88. The neck 78 of ferrule 74 is sized relative to receiving formation 88 such that the diameter of the cylindrical neck portion 78 is larger than the diameter of the smallest frustoconical portion defined by surface 86. Accordingly, when ferrule 74 is received in receiving formation 88, the outer circular edge 79 of cylindrical neck portion 78 will engage the frustoconical surface 86 resulting in circular, line contact between ferrule 74 and surface 86.

To use connector 10, spring 54 and follower 56 are received in the cylindrical chamber 52 formed by cap 12. Cap 12 is then threaded onto base 22. Once cap 12 has been secured to base 22, spring 54 and follower 58 are retained in the assembly by means of web 28 which acts as a stop. Conduit 70 is then fed through opening 18 and passageway 68, end 72 being fitted with ferrule 74. Base 22 is then connected to second conduit 40 by means of the bayonet mount described above which results in ferrule 74 being received in receiving formation 88. Because of the biasing action of spring 54, follower 58 is urged in a direction away from end wall 16 and toward stop 28. This results in a biasing force being transmitted to ferrule 74 through annular boss 66 which in turn urges circular periphery 79 of cylindrical neck portion 78 into engagement with surface 86. Because of the biasing action of spring 54, regardless of the expansion and/or contraction that ferrule 74 and first conduit 40 may undergo during temperature cycling from ambient temperature to elevated temperatures of 100° to 400° C., ferrule 74 remains in sealing engagement with surface 86. This sealing between ferrule 74 and surface 86 is enhanced by the deformable nature of the material of ferrule 74, particularly at elevated temperatures.

It will be appreciated that in order to achieve the line contact desired between the ferrule 74 and the surface 86, surface 86 must be tapered in some fashion and preferably is frustoconical. Ferrule 74 can be either frustoconical or cylindrical, or for that matter various other shapes provided that at the point of engagement between the ferrule 74 and surface 86, ferrule is circular when viewed in transverse cross section so as to ensure substantially circular, line contact between the ferrule and the surface. In the embodiment shown in FIG. 2, since the diameter of the cylindrical neck portion 78 is larger than the smallest diameter of the frustoconical receiving formation 88, the outer peripheral, circular edge 79 of neck portion 78 wil surface 86 in such line contact. At the same time, frustoconical portion 76 of ferrule 74 will be spaced from surface 86. It will be appreciated that ferrule 74 need not have the shape shown in FIG. 2 but could be cylindrical and various other shapes, the only necessity being that whatever the shape, ferrule 74 be shaped and sized to accommodate the line contact discussed above. For example, both ferrule 74 and receiving formation 88 could be frustonical in shape provided that surface 86 flares outwardly at a greater angle than the frustoconical surface of ferrule 74.

The connector 10 thus provides a means to provide fluid-tight communication between the bore formed in a first conduit, i.e., bore 84 in conduit 40 and the bore in conduit 70. The connector is effective at high temperatures or after being cycled to much lower temperatures since, at all times biasing action of the spring will maintain the ferrule in contact with the surface 86 to accommodate changes in expansion and contraction of the materials of the ferrule and the first conduit.

While the biasing means is shown as a quartz spring 54, it will be recognized that other means of biasing the follower 56 can be employed. Use of a quartz spring has particular advantage when the connector is to be used in very high temperature environments where metallic springs might fail.

It will be recognized that the means of attachment between cap 12 and base 22 and base 22 and first conduit 40 need not be as shown. For example, threaded connection between cap 12 and base 22 could be replaced with some quick disconnect assembly as, for example, the bayonet mount used to connect base 22 to first conduit 40. Likewise, base 22 could be attached to first conduit 40 by threads if desired. Other means of releasably attaching the cap, the base and the first conduit together could also be employed and will be apparent to those skilled in the art.

As noted above, ferrule 40 is preferably made of a deformable material. The term "deformable" as used herein refers to a material which, under compression, deforms to the extent necessary to achieve a gas-tight seal between the ferrule and the engaged surface, considering line contact between the ferrule and the surface. Suitable materials for use in forming the ferrule include polyamides, polyimides and various other polymeric materials which are generally not considered to be elastic but are formable as that term is used above. The provision by the connector of the present invention of substantial line contact sealing between the ferrule and the surface 86 obviates the necessity for machining parts to extremely close tolerances in an attempt to achieve mated, gas-tight engagement between relatively large surfaces.

The foregoing disclosure and description of the invention is illustrative and explanatory thereof, and various changes in the size, shape and materials as well as in the details of the illustrated construction may be made within the scope of the appended claims without departing from the spirit of the invention.

What is claimed is:

1. An apparatus for connecting a first conduit having a first bore to a second conduit having a second bore to provide communication between said first and second bores comprising:
   a base;
   means to attach said base to said first conduit;
   a cap, said second conduit extending through said cap;
   means to attach said cap to said base;
   a follower slidably disposed in said cap, said follower having a passageway therethrough, said second conduit extending through said passageway;
   a ferrule received on said second conduit, said ferrule having a first end and a second end;
   biasing means operative to urge said follower against said first end of said ferrule;
   said first bore in said first conduit having a frustoconical surface defining receiving formation for said ferrule, said ferrule second end of said having a portion which is circular when viewed in transverse cross section such that when said second end of said ferrule is urged into said receiving formation by said biasing means, said ferrule engages said frustoconical surface defining said receiving formation in substantially line contact.

2. The apparatus of claim 1 wherein said second conduit comprises a quartz capillary tube.

3. The apparatus of claim 1 wherein said first conduit comprises a fused quartz member.

4. The apparatus of claim 1 wherein said means to attach said base to said first conduit comprise a bayonet mount.

5. The apparatus of claim 1 wherein said cap is threadedly attached to said base.

6. The apparatus of claim 1 wherein said base includes stop means to limit the movement of said follower away from said biasing means.

7. The apparatus of claim 1 wherein said biasing means comprises a fused quartz spring, the spring being disposed interiorly of said cap between a stop wall formed on said cap and said follower.

8. The apparatus of claim 1 wherein said ferrule is comprised of a heat resistant, deformable material.

9. The apparatus of claim 1 wherein said ferrule has a frustoconical portion and a cylindrical portion, said cylindrical portion defining said second end of said ferrule, said cylindrical portion of said ferrule engaging said frustoconical surface of said receiving formation to thereby space said frustoconical portion of said ferrule from said surface defining said receiving formation.

* * * * *

UNITED STATES PATENT AND TRADEMARK OFFICE
CERTIFICATE OF CORRECTION

PATENT NO. : 4,991,883

DATED : February 12, 1991

INVENTOR(S) : Raymond D. Worden

It is certified that error appears in the above-identified patent and that said Letters Patent is hereby corrected as shown below:

In column 5, Claim 1, line 23, after "defining" insert --a--.

In column 5, Claim 1, line 24, delete "ferrule second end of said" and insert therefor --second end of said ferrule--.

Signed and Sealed this

Twenty-first Day of July, 1992

Attest:

DOUGLAS B. COMER

Attesting Officer

Acting Commissioner of Patents and Trademarks